US009737466B2

(12) United States Patent
Devore et al.

(10) Patent No.: US 9,737,466 B2
(45) Date of Patent: Aug. 22, 2017

(54) LONG LASTING BREATH MINT

(71) Applicant: NeuOra Microceuticals, LLC, Murray, UT (US)

(72) Inventors: Greggory R. Devore, La Canada, CA (US); James W. Devore, Westlake, OH (US); Douglas C. Pratt, Gig Harbor, WA (US); Steven A. Devore, Orem, UT (US)

(73) Assignee: Neuora Microceuticals, LLC, Murray, UT (US)

( * ) Notice: Subject to any disclaimer, the term of this patent is extended or adjusted under 35 U.S.C. 154(b) by 71 days.

(21) Appl. No.: 14/988,385

(22) Filed: Jan. 5, 2016

(65) Prior Publication Data

US 2016/0158117 A1     Jun. 9, 2016

Related U.S. Application Data

(62) Division of application No. 14/276,905, filed on May 13, 2014, now abandoned.

(51) Int. Cl.

| | | |
|---|---|---|
| *A61K 9/20* | (2006.01) | |
| *A61K 9/36* | (2006.01) | |
| *A61K 8/02* | (2006.01) | |
| *A61K 8/97* | (2017.01) | |
| *A61K 8/73* | (2006.01) | |
| *A61Q 11/00* | (2006.01) | |
| *A61K 9/00* | (2006.01) | |
| *A61K 8/04* | (2006.01) | |
| *A61K 8/34* | (2006.01) | |
| *A61K 8/60* | (2006.01) | |

(52) U.S. Cl.
CPC .......... *A61K 8/0245* (2013.01); *A61K 8/0216* (2013.01); *A61K 8/0233* (2013.01); *A61K 8/042* (2013.01); *A61K 8/345* (2013.01); *A61K 8/60* (2013.01); *A61K 8/731* (2013.01); *A61K 8/733* (2013.01); *A61K 8/97* (2013.01); *A61K 9/006* (2013.01); *A61K 9/0056* (2013.01); *A61K 9/205* (2013.01); *A61K 9/2054* (2013.01); *A61Q 11/00* (2013.01); *A61K 2800/592* (2013.01); *A61K 2800/652* (2013.01)

(58) Field of Classification Search
None
See application file for complete search history.

(56) References Cited

U.S. PATENT DOCUMENTS

| | | | |
|---|---|---|---|
| 3,857,964 A | 12/1974 | Yolles | |
| 4,259,314 A | 3/1981 | Lowey | |
| 5,284,659 A | 2/1994 | Cherukuri et al. | |
| 5,624,677 A | 4/1997 | El-Rashidy et al. | |
| 5,942,244 A | 8/1999 | Friedman et al. | |
| 6,210,699 B1 | 4/2001 | Acharya et al. | |
| 6,428,827 B1 | 8/2002 | Song et al. | |
| 7,569,605 B2 | 8/2009 | Jonas et al. | |
| 8,236,348 B2 | 8/2012 | Gin et al. | |
| 8,653,066 B2 | 2/2014 | Bosse | |
| 2003/0152629 A1 | 8/2003 | Shefer et al. | |
| 2004/0115137 A1* | 6/2004 | Verrall | A61K 8/0208 424/48 |
| 2004/0247647 A1 | 12/2004 | Ivory et al. | |
| 2008/0193526 A1 | 8/2008 | Pettersson et al. | |
| 2009/0081294 A1 | 3/2009 | Gin et al. | |
| 2012/0288548 A1 | 11/2012 | Boyd et al. | |
| 2013/0101652 A1 | 4/2013 | Boyd et al. | |
| 2013/0216648 A1 | 8/2013 | Lenzi et al. | |

FOREIGN PATENT DOCUMENTS

| | | |
|---|---|---|
| EP | 0437098 A2 | 7/1991 |
| WO | WO2004014346 A1 | 2/2004 |
| WO | WO2007139661 A1 | 12/2007 |
| WO | WO2010132126 A1 | 11/2010 |
| WO | WO2013090452 A1 | 6/2013 |

OTHER PUBLICATIONS

Neuora Microceuticals, "ForeverMints: Science Has Finally Created a Breath Mint That Lasts for Hours", www.forevermints.com, Dec. 31, 2013.
Iqbal, Z. et al., "Preparation and in-vitro evaulation of sustained release matrix diclofenac sodium tablets using HPMC KM 100 and gums", Archives of Pharmacy Practice, 2010, p. 917, vol. 1, No. 2.
European Patent Office, International Search Report and Written Opinion for PCT/US2014/027919, Nov. 3, 2014.
Devore, James et al., "Slow-Dissolving Oral Compositions", U.S. Appl. No. 14/271,793 filed May 7, 2014, Publisher: Not yet published.
Viriden, A. et al., "The effect of chemical heterogeneity of HPMC on polymer release from matrix tablets", European Journal of Pharmaceutical Sciences, Nov. 13, 2008, pp. 392-400, vol. 36, Publisher: Elsevier.

* cited by examiner

*Primary Examiner* — Susan Tran
(74) *Attorney, Agent, or Firm* — Gable Gotwals

(57) ABSTRACT

A long lasting breath mint including a carrier and a flavorant, wherein the carrier includes at least one of a high viscosity cellulose ether and a low viscosity cellulose either and an alginate. The carrier forms a gel upon contact with saliva. A tablet is placed in the mouth of user, whereupon the tablet is wetted with saliva. A surface of the tablet is converted to a gel resulting in a tablet having an outer gel layer and a core. The gel serves as an adhesive for adhering the tablet to mouth structure. The gel slows exposure of the core to moisture and also slows diffusion of flavorant into the mouth of the user with the gel resulting in a breath mint having an extremely long life prior to complete dissolution, e.g., greater than 30 minutes or longer.

6 Claims, 1 Drawing Sheet

LONG LASTING BREATH MINT

CROSS REFERENCE TO RELATED APPLICATIONS

This application is a Divisional of U.S. patent application Ser. No. 14/276,905, filed May 13, 2014, titled, "LONG LASTING BREATH MINT," which claims the priority of U.S. Provisional Patent Application No. 61/822,909, filed May 13, 2013, titled "SLOW-DISSOLVING ORAL COMPOSITIONS," the contents of both of which are hereby incorporated by reference.

FIELD OF THE INVENTION

This application relates to breath mints. In particular, this application relates to a long lasting breath mint having a small size that is comfortable and unobtrusive in the mouth of a user for long periods of time.

BACKGROUND OF THE INVENTION

The quest for fresh breath spans over 4,000 years, including the chewing of spices—for example, cloves, anise (fennel) seeds, and cardamom, and herbs, for example, mint and parsley. Today, a vast array of chewing gum and candy mints are available for freshening breath and/or masking bad breath. Chewing gum has a negative public image in some societies, however, as well as the well-known problem of a limited flavor lifetime. The effectiveness of candy mints is limited by their lifetime in a user's mouth, which is often measured in minutes. Sugar is an ingredient in many candy mints, which promotes tooth decay and has a high glycemic index.

SUMMARY OF THE INVENTION

The long lasting breath mint of the invention is of a size and weight that can stay comfortably in place in the mouth of a user for long periods of time. The breath mint of the invention is preferably a tiny oral hydrophilic matrix time-release tablet that transforms to a gel over time. The gel facilitates and ability for the mint to stay comfortably in place in the mouth, adhering to the gum line, a partial, half dentures, full dentures or complete natural teeth, for 30 minutes to several hours, while dissolving. As the breath mint dissolves, the mint continuously releases and delivers flavor and ingredients, causing salivation and naturally refreshing the breath. In one embodiment, the mint additionally includes enhancements, such as Vitamin D, chromium picolinate, Xylitol, Vitamin B complex, melatonin, or other enhancements.

Compositions and methods of manufacturing provide slow-dissolving oral compositions, which permit the manufacture of dramatically smaller dosage forms than have been heretofore possible. For example, embodiments of the oral compositions in the form of microtablets adhere to a user's gum and dissolve over at least about 2 hours, whereas previous formulations would require tablets of over twice the weight to obtain the same lifetime. In some embodiments, a size, shape, and feel of the microtablet when adhered to a user's gum is so comfortable to the user as to be easily ignored, for example, while speaking. Some embodiments of the composition comprise at least one cellulose ether and alginate. Some embodiments are useful for freshening breath and/or reducing dry mouth. Some embodiments provide slow release of nutritional supplements, vitamins, or the like.

The flavorant of the invention is designed such that it allows a small amount of natural flavor in each tablet to pack a pleasant, cooling and long-lasting mint flavor or other flavor, greatly amplifying and extending this effect for the full multi-hour duration of the tablet.

Some embodiments provide method for freshening breath comprising administering the breath mint that adheres to a user's gum.

The breath mint of the invention uses ingredients that may be in powder or liquid form. In one embodiment, the powder form utilizes materials of various viscosities, particle size and particle size distributions that are mixed together. A direct compression method may be used to form the raw materials into tablets. In one embodiment, the powdered raw material utilizes different ingredients that range in size from 50 μm to 1190 μm in size. A variation in particle size falling between a ratio of 1 and 24 results in improved flow during the formation and tablet forming process. The particle sizes may further fall between ratios of 1:16, 1:8, and 1:2.

A direct compression method is the preferred method to form tablets. Direct compression manufacturing equipment can range from small bench type models to large computerized models. Examples of some of the current manufacturers of direct compression tablet presses include: Stokes, Fette Compacting, Korsch, Kikusui, Manesty, B&D, IMA, Courtoy, and International Process and Packaging Technologies (IPPT). Typically, tablets formed from these presses are formed using pressures of 200-10,000 PSI. The ideal compression strength to produce a tablet depends on a variety of variables such as viscosity of materials, selection of binders, size of tablet being formed, and the number of tablets being formed at the same time. The above-mentioned list is just a few of the variables that must be evaluated in the compression cycle to produce a tablet for an intended application.

The breath mint of the invention may be of various geometric shapes that fit comfortably in the mouth of a user. Example shapes include oval, round, flat, semi-flat, spherical, semi-spherical, triangular, semi-triangular, pyramid, and diamond. Other shapes may also be utilized.

One component of the mint of the invention is a binder. The selection of binder materials is critical to the production of a small long lasting breath mint that dwells unobtrusively in the mouth of a user. By selecting materials from various families of saccharides and their derivates, synthetic binders, and incorporating various gums, gelatins, and alginates and then by varying their molecular weights and viscosities, a carrier was developed that formed a gel upon contact with moisture.

Certain members of the family of polysaccharides (methycellulose (MC), hydroxypropylcellulose (HPC), hydroxypropylmethycellulose (HPMC) and others), gums, gelatins, and alginates contain hydrophillic side chains that partially dissolve to form a soft, weak hydrogel upon contact with water. By selecting the correct combinations of the above materials, the tablet of the invention generates a gel surface on the tablet after exposure of about a minute to the saliva of the mouth. The creation of this gel layer provides several desirable features including adhesion to mouth surfaces and long life of the mint by controlling a rate of dissolution of the mint core.

In some embodiments, the microtablet forms a segmented tablet in contact with moisture, the segmented tablet comprising an outer gel layer and a solid core.

The outer gel layer produced on the surface of the tablets upon exposure to saliva is moldable to selected mouth structure to achieve a complementary shape to adjacent mouth structures, which aids in placement of the tablet and provides the right amount of adhesion to a selected area of the mouth of a user without causing an unpleasant gummy mess within the mouth.

The outer gel layer controls the rate and the extent of exposure of the tablet core to moisture, thereby slowing the rate and extent of dissolution. The correct combinations of carriers and flavorants, combined with the correct compression during tablet formation results in tablets that slowly melt away over a minimum of thirty minutes up to several hours. The dissolution rate is dependent upon the selection and amount of binders that are used to compliment the active ingredients. The formation of the gel surface slows the dissolution process of the tablets as confirmed by paddle dissolution testing. The tablet of the invention preferably results in a minimum dwell time of thirty minutes. Even when sucked on in the oral cavity like other mints, the tablets of the invention melt over a thirty to ninety minute period and continuously deliver a pleasant flavor.

In one aspect of the invention, the composition dissolves in more than about 30 minutes as measured by a paddle test, in an aspect, the composition dissolves in more than about two hours as measured by a paddle test and, in an aspect of the invention, the composition dissolves in more than about four hours as measured by a paddle test.

The gel layer controls the rate and extent of penetration of moisture into the tablet and the rate and extent of migration of active ingredients out of the tablet to their target tissues. The penetration of saliva (moisture) into the matrix of the tablet and that migration of active ingredients out of the tablet is controlled by diffusion across concentration gradients. The first concentration gradient is between the saliva (moisture) of the mouth and the solid surface of the tablet. As saliva (moisture) is pulled into tablet a second concentration gradient is created at the tablet—saliva interface in the form of a gel. The formed gel has a lower concentration of active ingredients than the solid phase of the tablet but a higher concentration than the surrounding saliva (moisture) of the mouth. The gel's lower concentration of active ingredients results in a slowing of the diffusion process out of the tablet as explained by Fick's first law of diffusion and Chatelier's principle of equilibrium. Again, by choosing the right combination of binders and active ingredients, we are able to create the correct set of parameters that produce the gel with a desirable permeability.

The binder material is selected to not mask or impede a long lasting and appealing effect from the flavorant. By mixing appropriately selected carriers with a particular flavorant, an appropriate combination may be obtained that does not produce too powerful a flavor that could be offensive and potentially irritating to the oral mucosa. At the same time, sufficient flavor should be delivered to be pleasant to the taste and effective as a breath freshener.

By using a combination of binders in the tablet of the invention, i.e. saccharides, certain polysaccharides (MC, HPC, HPMC, etc.), gums, gelatins, and alginates, tablets may be created of various sizes and shapes that fit comfortably between the gum and cheek. Several forms and sizes fit well within this space of the mouth. Since the tablet surface forms a gel within minutes of being placed in the mouth, the tablet contours to the surface where it has been placed, allowing a user to locate the mint in the most comfortable location and in a location that is imperceptible to anyone other than the user.

Some embodiments include at least one flavorant. In some embodiments, the at least one flavorant includes peppermint. In some embodiments, the at least one flavorant includes xylitol. In some embodiments, the at least one flavorant includes N-ethyl-p-menthane-3-carboxamide.

By choosing the correct gel forming carriers to combine with matching flavors, the extent of the duration of the flavor emitting from the gel surface of the tablet may be matched for the duration of the dwell time of the tablet, e.g., from a minimum of thirty minutes to several hours. Not only does the gel control the release of the flavor but also the extent of the flavorant delivered, so the flavor derived from the tablet is neither diminished nor released in excess.

Carriers are selected that compliment particular enhancements, to enable the tablet of the invention additionally deliver the enhancements over an extended period and at a rate that allows for the optimal absorption of the enhancements through the oral mucosa. In combination with appropriate flavorants, any negative tastes that are inherent to the enhancements may be masked.

Some embodiments provide a slow-dissolving oral composition comprising a carrier comprising at least one cellulose ether and alginate. Some embodiments comprise from about 10% to about 60% by weight of the at least one cellulose ether and from about 40% to about 90% of the alginate.

Some embodiments provide a microtablet comprising a slow-dissolving oral composition comprising a carrier comprising at least one cellulose ether and alginate, wherein the microtablet, when adhered to a user's gum, dissolves over at least about 2 hours.

In some embodiments, the enhancement comprises at least one nutritional supplement. In some embodiments, the at least one nutritional supplement includes vitamin D3. In some embodiments, the at least one nutritional supplement includes chromium picolinate. In some embodiments, the microtablet is a breath mint. Some embodiments further comprise a nutritional supplement.

In some embodiments, the breath mint includes a flavorant, a sweetener, a neutraceutical, a beneficial agent or combinations thereof. In some embodiments, the flavorant is peppermint. In some embodiments, the sweetener is xylitol. In some embodiments, the neutraceutical is vitamin D3 and in some embodiments, the neutraceutical is chromium picolinate.

Preferred polysaccharides of the family of polysaccharides for the breath mint of the invention have a viscosity between 2 mPa's to 40,000 mPa's and 60,000 mPa's to 150,000 mPa's can be composed of either a high viscosity or low viscosity hydroxypropyl methylcellulose alone or a combination of either.

In one aspect, the carrier comprises (i) from about 30 to about 60 wt. % of a high viscosity hydroxypropyl methylcellulose (HMPC), in some embodiments from about 35 to about 55 wt. % of the high viscosity HMPC and, in some embodiments, from about 40 to about 50 wt. % of the high viscosity HMPC, (ii) from about 10 to about 40 wt. % of a low viscosity HMPC, in some embodiments, from about 15 to about 35 wt. % of the low viscosity HMPC, and in some embodiments from about 20 to about 30 wt. % of the low viscosity HMPC, (iii) from about 0.5 to about 25 wt. % of hydroxypropylcellulose (HPC), in some embodiments, 1 to about 20 wt. % of the HPC and in some embodiments, from about 5 to about 25 wt. % of the HPC and (iv) from about 5 to about 35 wt. % of an alginate, in some embodiments, in some embodiments, from about 10 to about 30 wt. % of the alginate and, in some embodiments, from about 15 to about 25 wt. % of an alginate, based on the weight of the carrier, where the total of the wt. %'s of (i)-(iv) equals 100.

In some embodiments, a weight of the microtablet is not greater than about 145 mg. In some embodiments, a diameter of the microtablet is not greater than about 6.4 mm (0.25 inch).

In one embodiment, an example weight of the tablet is between 50 mg to 350 mg.

In accordance with one aspect of the invention, the breath mint tablet, comprises (a) from about 10 to about 60 wt. % of a carrier, in some embodiments from about 20 to about 50 wt. % of a carrier, and in some embodiments from about 30 to about 40 wt. % of a carrier, (b) from about to about 40 to about 90 wt. % of an active ingredient; in some embodiments, from about to about 50 to about 80 wt. % of an active ingredient and, in some embodiments, from about 60 to about 70 wt. % of an active ingredient and (c) from 0 to about 20 wt. % of at least one conventional additive, based on the weight of the composition.

In some embodiments, the composition weighs from about 250 to about 130 mg, in some embodiments, the composition weighs from about 150 to about 135 mg, and in some embodiments, the composition weighs from about 170 to about 132.5. The weight of the mint is governed by the ability of the mint to be form fitting to a desired location in the mouth for remaining securely in place. The activated gel layers overcome resistive force caused by the weight of the mint applied to the contact area to keep the mint in static equilibrium. Therefore, the mass is preferably directly proportional to the adhesion force to keep the mint from moving.

BRIEF DESCRIPTION OF THE DRAWINGS

The accompanying drawings, together with the specification, illustrate exemplary embodiments, and together with the description serve to explain the principles of these embodiments.

DETAILED DESCRIPTION OF THE
PREFERRED EMBODIMENTS

Particular embodiments of the invention are described below in detail for the purpose of illustrating its principles and operation. However, various modifications may be made, and the scope of the invention is not limited to the exemplary embodiments described below.

As used in the specification and the appended claims, the singular forms "a," "an," and "the" include plural referents unless the context clearly dictates otherwise. Thus, for example, reference to "a flavoring agent" or "a colorant" encompasses a combination or mixture of different flavoring agents or colorants as well as a single flavoring agent or colorant.

Embodiments of compositions disclosed herein provide exceptionally small oral dosage forms with long lifetimes. For example, some embodiments provide a slow-dissolving breath mint in the form of a microtablet with a diameter not greater than about 6.4 mm (0.25 inch) and a weight not greater than about 141 mg, which dissolves over at least about 2 hours when adhered to a user's gum, releasing flavor, freshening a user's breath, and moistening the user's mouth over the lifetime thereof. In contrast, typical slow release breath mints with similar lifetimes have over twice the weight. Furthermore, lifetimes of candy mints and the flavor release of chewing gums are typically measured in minutes rather than hours. Some embodiments of the microtablet further comprise enhancements, such as a nutritional supplement, a vitamin, a mineral, a coenzyme, a biologically active compound, or a combination thereof.

Figure 2:
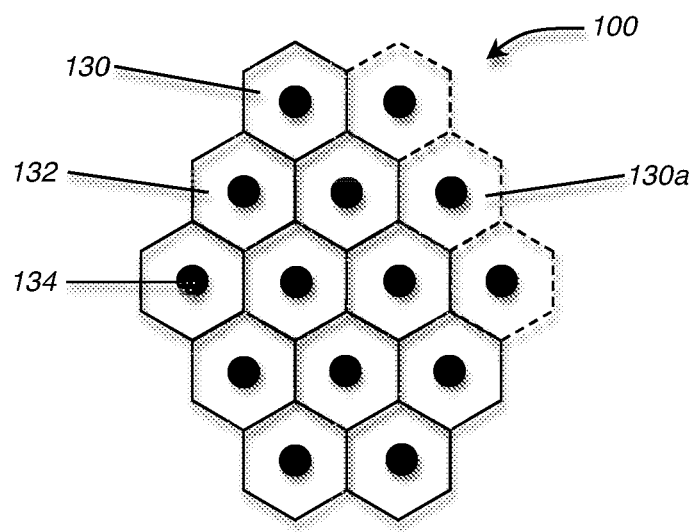
FIG. 2 schematically illustrates an embodiment of a microstructure of the compressed tablet of FIG. 1.

FIG. 2 schematically illustrates a proposed structure of an embodiment of the microtablet 100. Without being bound by any theory, it is believed that each microtablet 100 comprises microscopic honeycomb-like cells 130. As illustrated in FIG. 2, each cell 130 comprises a carrier layer 132, which includes a carrier, and a nucleus 134, which includes substantially all of the one or more active ingredients. The carrier in the carrier layer 132 forms the gel layer 110 when contacted by moisture from a user's saliva. Cells 130 on the surface of the microtablet 100 protect cells 130 in the interior from the user's saliva. In FIG. 2, surface cells 130a in the process of dissolving are indicated by dashed lines. The active ingredients in the nucleus 134 remain dispersed in the gel layer 110, and become exposed to the user as the outer surface of the gel layer 110 dissolves in the user's mouth. Consequently, the microtablet 100 exhibits a slow or controlled release of the active ingredients in the nucleus 134 and a long lifetime for the microtablet 100.

In some embodiments, the carrier comprises at least one cellulose ether and alginate. As discussed above, the carrier forms an adhesive gel in contact with moisture. In some embodiments, the composition comprises from about 19% to about 39% percent of the carrier by weight. In some embodiments, the composition comprises from about 16% to about 32% of the at least one cellulose ether, and from about 3% to about 7%, of the alginate.

Examples of suitable cellulose ethers include, for example, methylcellulose, ethylcellulose, hydroxypropyl methylcellulose (hypromellose, HPMC), carboxymethylcellulose, hydroxyethylcellulose, hydroxypropylcellulose (HPC), and the like, and combinations thereof. Some embodiments, comprise hydroxypropyl methylcellulose. Some embodiments comprise hydroxypropyl methylcellulose and another cellulose ether.

Examples of suitable alginates include sodium alginate, potassium alginate, alginic acid, algin, and combinations thereof. It is believed that the alginate contributes to the adhesion of the microtablet to the user's gum.

In some embodiments, the active ingredient includes at least one flavorant. The at least one flavorant is of any type known in the art, for example, essential oils, natural flavorants, artificial flavorants, nature-identical flavorants, semi-synthetic flavorants, and the like. The at least one flavorant provides the composition with a desired flavor profile, for example, mint (spearmint), peppermint, cinnamon, wintergreen, licorice, citrus, lemon, orange, lime, vanilla, chocolate, strawberry, cherry, ginger, banana, and the like. Because flavor preferences vary by geography and/or culture, some embodiments of the composition comprise flavor profiles selected accordingly. Examples of suitable flavorants include menthol (peppermint) R-(−)-carvone (spearmint), methyl salicylate (wintergreen), cinnamaldehyde (cinnamon), anethole (hcorice/anise), vanillin (vanilla), and the like. In some embodiments, the at least one flavorant gives the composition breath freshening properties. In some embodiments, the at least one flavorant masks an undesired taste of another ingredient in the composition.

In some embodiments, the at least one flavorant includes at least one sweetener. Suitable sweeteners include natural sweeteners and artificial sweeteners. Suitable natural sweeteners include sugars, monosaccharides, disaccharides, sugar alcohols, and other natural sweeteners, for example, glucose, fructose, sucrose, xylitol, sorbitol, and *stevia*. Suitable artificial sweeteners include, for example, aspartame, sucralose, neotame, acesulfame, potassium, and saccharin. In some embodiments, the at least one sweetener includes xylitol, which has a low glycemic index, is non-cariogenic (does not promote tooth decay). In some embodiments, the at least one sweetener is xylitol.

In an aspect of the invention, a slow dissolving breath mint comprises (a) from about 10 to about 60 wt. % of a carrier, (b) from about to about 90 to about 40 wt. % of an active ingredient and (c) from 0 to about 20 wt. % of at least one conventional additive, based on the weight of the composition. In an aspect of the invention, the slow dissolving breath mint comprises (a) from about 20 to about 50 wt. % of the carrier, (b) from about to about 80 to about 50 wt. % of the active ingredient and (c) from 0 to about 20 wt. % of the at least one conventional additive, based on the weight of the composition. And in an aspect of the invention, the slow dissolving breath mint comprises (a) from about 30 to about 40 wt. % of the carrier, (b) from about to about 70 to about 60 wt. % of an active ingredient and (c) from 0 to about 20 wt. % of at least one conventional additive, based on the weight of the composition.

In one embodiment, the mint of the invention includes an enhancement that is a sensate agent. Sensate agents provide cooling, tingling, heat or the like. Representative cooling agents include, without limitation, carboxamides, menthol and ketals, and diols. In one aspect the cooling agent is a paramenthan carboxyamide agent, such as N-ethyl-p-menthan-3-carboxamide, known commercially as "WS-3", N,2,3-trimethyl-2-isopropylbutanamide, known as "WS-23," and mixtures thereof. Additional cooling agents include menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. Representative heating agents include, without limitation, capsaicin. Representative tingling agents include, include without limitation, cinnammic aldehyde.

The breath mint of the invention may be in the form of a microtablet (microtab), tablet, lozenge, pastille, troche, or dragee. In some embodiments, a microtablet is manufactured by directly compressing a powder form of the composition between dies. In some embodiments, the microtablet is coated, while in other embodiments the microtablet is uncoated.

To provide contact for the user, the breath mint of the invention is of a small size. In one embodiment, a longest dimension of the microtablet is about 10 mm, about 9 mm, about 7 mm, about 6 mm, 5 mm, or about 4 mm. In some embodiments, the microtablet has a diameter of about 6.4 mm (0.25 in). In some embodiments, a thickness of the microtablet is about 5 mm, about 4.9 mm, about 4.8 mm, about 4.7 mm, about 4.6 mm, about 4.5 mm, about 4.4 mm, about 4.3 mm, about 4.2 mm, about 4.1 mm, or about 4 mm. The microtablet dimensions or size is preferably sufficiently small to comfortably fit entirely between a user's inner cheek and gum. Preferably, the microtablet is sized sufficiently small as to be unnoticed by the user over its lifetime when adhered to the user's gum, for example, while speaking. The adhesion of the microtablet adheres to the user's gum to reduce migration thereof.

Some embodiments of the microtablet have a mass of less than about 250 mg, less than about 200 mg, less than about 190 mg, less than about 180 mg, less than about 170 mg, less than about 160 mg, less than about 155 mg, less than about 150 mg, less than about 145 mg, less than about 144 mg, less than about 143 mg, less than about 142 mg, less than about 141 mg, less than about 140 mg, less than about 139 mg, less than about 138 mg, less than about 137 mg, less than about 136 mg, less than about 135 mg, less than about 134 mg, less than about 133 mg, less than about 132 mg, less than about 131 mg, or less than about 130 mg.

In some embodiments, when the microtablet is adhered to a user's gum, it dissolves over the course of at least 30 minutes, at least one hour, at least two hours, at least three hours, at least four hours, at least five hours, at least six hours, at least seven hours, at least eight hours, at least nine hours, or at least ten hours. In some embodiments, the microtablet dissolves at a faster rate when administered in a different manner, for example, in a user's mouth but not adhered to the gum, where a user is likely to suck on the microtablet. For example, some embodiments that take at least about 2 hours to dissolve when adhered to the gum dissolve over from about 30 minutes to about 90 minutes when not adhered to the gum. In some embodiments, this slow dissolution or long lifetime of the microtablet provides a slow or extended release of one or more active ingredients thereof, for example, a flavor component or enhancement. Suitable flavor components include, for example, flavorants and/or sweeteners. Other examples of suitable active ingredients include enhancements, such as nutritional supplements, vitamins, minerals, co-factors, biologically active compounds, and the like.

In some embodiments, the active ingredient is a probiotic product making up 30 wt. % to 90 wt. % of the composition in addition to a minimum of 1 wt. % to 3 wt. % or greater of flavorant.

Figure 1:
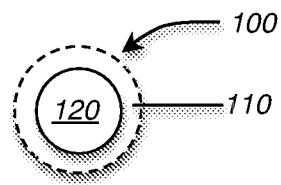
FIG. 1 schematically illustrates an embodiment of a compressed tablet of the invention.

In some embodiments, moisture from a user's saliva activates an adhesive that allows the microtablet to adhere to the gum and converts a surface of the microtablet 100 into a gel layer 110, as illustrated in FIG. 1, thereby generating a segmented gel comprising an outer gel layer 110 and a solid core 120. In some embodiments, the gel layer 110 forms over the course of from about 30 minutes to about 1 hour. As the microtablet 100 dissolves, the core 120 shrinks, the outer surface thereof adding to the gel layer 110 as illustrated in FIG. IB. The gel layer 110 has several functions. The gel layer 110 improves the mouth-feel of the microtablet 100, when attached to a user's gum, over the course of its several-hour lifetime compared with a completely solid formulation by cushioning the solid core 120 from the user's mouth, thereby contributing to the comfort of the microtablet. The gel layer 110 is also believed to control moisture diffusion from a user's mouth to the core 120, thereby preventing premature disintegration of the microtablet 100, and therefore is at least partially responsible for the long lifetime of the microtablet. The gel layer 110 controls diffusion of the one or more active ingredients into the user's mouth, and consequently, provides controlled release of flavor components, resulting in long-lasting flavor. In some embodiments, the gel layer 110 also adheres the microtablet to the user's mucosa and/or gum.

In some embodiments of the composition, enhancements may be provided, such as at least one nutritional supplement, vitamin, mineral, coenzyme, biologically active compound, or the like. Examples include acetyl L-carnitine, boswellia *serrata* extract, boswellia serrate resin, astaxanthin, benfotiamine, beta glucan, bergamot, black *catechu* heartwood, black currant, black rice, blueberry, boron, bromelain, calcium fructoborate, caffeine, chamomile, chinese skullcap root, chromium piccolinate, chondroitin sulfate, citrulline, cocoa, coenzyme Q10, copper glycinate, *cordyceps*, cranberry seed oil, curcumin, dang shen, DHA (docosahexaenoic acid), eleutherococcus senticosus, EPA (eicosapentaenoic acid), boswellia *serrata* extract, fisetin, vitamin B9, calcium fructoborate, γ"amino butyric acid, gamma tocopherol, glucosamine sulfate, grape seed, holy basil, hops strobile, hydrolyzed milk protein, krill oil, L-carnosine, lemon balm, L-arginine, L-theanine, lutein, magnesium, marigold flower, melatonin, curcumin phospholipid (Meriva® curcumin phytosome, Thorne Research, Dover, Id.), methylsufonylmethane, n-acetylcysteine, nattokinase, niacin, niacinamide, omega-3 fatty acids, omega-6 fatty acids, omega-7 fatty acids, omega-9 fatty acids, low molecular weight polyphenol (Oligonol®, Amino Up Chemical, Japan), *Panax ginseng*, phosphatidylserine complex, pomegranate seed oil, potassium, quercetin, reishi, resveratrol, *Rhodiola rosea* (golden root), rutin, *Salvia miltiorrhiza*, sea buckthorn oil, Siberian *ginseng*, squid oil, taurine, tocopherols, tocotrienols, trypsin, turmeric, UC-II undenatured-type 2 collagen, *Scutellaria baicalensis* and *Acacia catechu* bioflavonoid extract (Univestin®, Unigen, Seattle, Wash.), valerian root, vitamin B complex, vitamin B3, vitamin B6, vitamin B12, vitamin C, vitamin D3, zeaxanthin, and zinc.

Some embodiments comprise an agent that provides a sensation to the user's mouth, for example, heating or cooling. An example of a heating agent is capsaicin. An example of a cooling agent is N-ethyl-p-menthane-3-carboxamide.

Some embodiments of the composition comprise other ingredients, for example, release agents, anti-caking agents, lubricants, and the like.

In an aspect of the invention, the carrier comprises (i) from about 30 to about 60 wt. % of a high viscosity hydroxypropylmethylcellulose (HPMC), (ii) from about 10 to about 40 wt. % of a low viscosity HMPC, (iii) from about 0.5 to about 25 wt. % of hydroxypropylcellulose (HPC), and (iv) from about 5 to about 35 wt. % of an alginate based on the weight of the carrier, where the total of the wt. %'s of (i)-(iv) equals 100. In an aspect of the invention, the carrier comprises (i) from about 35 to about 55 wt. % of the high viscosity HMPC, (ii) from about 15 to about 35 wt. % of the low viscosity HMPC, (iii) from about 1 to about 20 wt. % of the HPC and (iv) from about 10 to about 30 wt. % of the alginate where the total of the wt. %'s of (i)-(iv) equals 100. And in an aspect of the invention, the carrier comprises (i) from about 40 to about 50 wt. % of the high viscosity HMPC, (ii) from about 20 to about 30 wt % of the low viscosity HMPC, (iii) from about 5 to about 15 wt. % of the HPC and (iv) from about 15 to about 25 wt. % of the alginate, where the total of the wt. %'s of (i)-(iv) equals 100.

In an aspect of the invention, the high viscosity HPMC is defined as one having a molecular weight of 60,000 or greater. Suitable high viscosity HPMC's include, without limitation, Dow Methocel® cellulose ethers E4M CR, E10M CR, K4M, K15M, and K100M. In another aspect of the invention, a low viscosity HPMC is defined as one having a molecular weight of 50,000 or less. Suitable low viscosity HPMC's include, without limitation, Dow Methocel® cellulose ethers E5, E15LV, E50LV, AND K100LV.

In an aspect of the invention suitable HPC's include Ashland Klucel Nutra D®. Examples of suitable alginates include sodium alginate, potassium alginate, alginic acid, algin, and combinations thereof.

In some embodiments, the formulation is manufactured by blending the components to provide a powder, which is converted into microtablets, for example, by direct compression. In some embodiments, the tableting is performed under a relatively high pressure. Consequently, in those embodiments, the ingredients of the composition are selected for compatibility with the tableting conditions.

In one aspect of the invention, the breath mint additionally contains a colorant and/or other conventional additives. Suitable colorants include natural colorants, e.g., pigments and dyes obtained from mineral, plant, and/or animal sources. Examples of natural colorants include red ferric oxide, yellow ferric oxide, annattenes, alizarin, indigo, rutin, and quercetin. Synthetic colorants may also be used and may include an FD&C or D&C dye, e.g., an approved dye selected from the so-called "coal-tar" dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a "lake" thereof, i.e., an aluminum or calcium salt thereof. Useful colorants may be food colorants in the "GRAS" (Generally Regarded As Safe) category.

Some embodiments of the composition comprise other conventional additives, for example, release agents, such as magnesium stearate, anti-caking agents, lubricants, and the like.

In an aspect of the invention, the breath mint is formulated as a tablet, lozenge, pastille, troche, or dragee.

It is another distinct advantage of the invention, that in one aspect, the dimensions or size of the compressed tablet is sufficiently small so that it comfortably fit entirely between a user's inner cheek and gum. And in some aspects, the compressed tablet is sized sufficiently small as to be unnoticed by the user over its lifetime when adhered to the user's gum, for example, while speaking.

In an aspect of the invention, the breath mint is slow dissolving as measured by a paddle test. By paddle test is meant the following protocol:

Paddle Test

Fill a 250 ml beaker containing a stir bar with 200 ml of deionized water at pH 6.4.

Place the beaker inside a water bath (for example, inside a 600 ml beaker filled with ca. 50 ml of water) equipped with a temperature measuring device) (for example, a thermometer taped to the inside of the 600 ml beaker).

Place the entire apparatus on a hot plate stirrer (for example, a Corning Hot Plate Stirrer (Model PC---220)) and stir at 60 cycles per minute until the temperature of the water bath is equilibrated to 37 C.

Once these conditions are stable (60 cycles/min, 37 C), place 40 mg of the sample and measure the time it takes for the sample to dissolve.

In some embodiments, the compressed tablet dissolves in more than 30 minutes, as measured by the paddle test; in some embodiments, the compressed tablet dissolves in more than one hour, as measured by the paddle test, in some embodiments, the compressed tablet dissolves in more than three hours, as measured by the paddle test, in some embodiments, the compressed tablet dissolves in more than four hours, as measured by the paddle test, in some embodiments, the compressed tablet dissolves in more than five hours, as measured by the paddle test, in some embodiments, the compressed tablet dissolves in more than six hours, as measured by the paddle test; in some embodiments, the compressed tablet dissolves in more than seven hours, as measured by the paddle test, in some embodiments, the compressed tablet dissolves in more than eight hours, as measured by the paddle test; in some embodiments, the compressed tablet dissolves in more than nine hours, as measured by the paddle test; and in some embodiments, the compressed tablet dissolves in more than five hours, as measured by the paddle test.

In an aspect of the invention, moisture from a user's saliva may cause the compressed tablet to adhere to the user's gum. Without wishing to be bound by a theory of the invention, as illustrated in FIG. 1, it is believed that the saliva converts the surface of the compressed tablet 100 into a gel layer 110, thereby generating a segmented gel comprising an outer gel layer 110 and a solid core 120. In some embodiments, the gel layer 110 forms over the course of from about 30 minutes to about 1 hour. As the compressed tablet 100 dissolves, the core 120 shrinks, the outer surface thereof adding to the gel layer 110 as illustrated in FIG. 2. The gel layer 110 has several functions. The gel layer 110 improves the mouth-feel of the compressed tablet 100, when attached to a user's gum, over the course of its several-hour lifetime compared with a completely solid formulation by cushioning the solid core 120 from the user's mouth, thereby contributing to the comfort of the compressed tablet. The gel layer 110 is also believed to control moisture diffusion from a user's mouth to the core 120, thereby preventing premature disintegration of the compressed tablet 100, and therefore is at least partially responsible for the long lifetime of the compressed tablet. The gel layer 110 controls diffusion of the one or more active ingredients into the user's mouth, and consequently, provides controlled release of flavor components, resulting in long-lasting flavor. In some embodiments, the gel layer 110 also adheres the compressed tablet to the user's mucosa and/or gum.

FIG. 2 schematically illustrates a proposed structure of an embodiment of the compressed tablet 100. Without being bound by any theory, it is believed that each compressed tablet 100 comprises microscopic honeycomb-like cells 130. As illustrated in FIG. 2, each cell 130 comprises a carrier layer 132, which includes a carrier, and a nucleus 134, which includes substantially all of the one or more active ingredients. The carrier in the carrier layer 132 forms the gel layer 110 when contacted by moisture from a user's saliva. Cells 130 on the surface of the compressed tablet 100 protect cells 130 in the interior from the user's saliva. In FIG. 2, surface cells 130a in the process of dissolving are indicated by dashed lines. The active ingredients in the nucleus 134 remain dispersed in the gel layer 110, and become exposed to the user as the outer surface of the gel layer 110 dissolves in the user's mouth. Consequently, the compressed tablet 100 exhibits a slow or controlled release of the active ingredients in the nucleus 134 and a long lifetime for the compressed tablet It is another distinct advantage of the compositions disclosed herein that they provide exceptionally small oral dosage forms with long lifetimes. For example, some embodiments provide a slow-dissolving breath mint in the form of a compressed tablet with a diameter not greater than about 6.4 mm (0.25 inch) and a weight not greater than about 141 mg, which dissolves over at least about 2 hours when adhered to a user's gum, releasing flavor, freshening a user's breath, and moistening the user's mouth over the lifetime thereof. In contrast, typical slow release breath mints with similar lifetimes have over twice the weight. Furthermore, lifetimes of candy mints and the flavor release of chewing gums are typically measured in minutes rather than hours.

In some embodiments, the compressed tablet dissolves at a faster rate when administered in a different manner, for example, in a user's mouth but not adhered to the gum, where a user is likely to suck on the compressed tablet. For example, some embodiments that take at least about 2 hours to dissolve when adhered to the gum dissolve over from about 30 minutes to about 90 minutes when not adhered to the gum. In some embodiments, this slow dissolution or long lifetime of the compressed tablet provides a slow or extended release of one or more active ingredients thereof, for example, a flavor components or a nutritional supplement. In some embodiments, a compressed tablet is manufactured by directly compressing a powder form of the composition between dies. In one aspect, the compressed tablet is coated, while in another aspect the compressed tablet is uncoated.

In an aspect of the invention, the compressed tablet is manufactured by blending the components in a suitable blender, such as a high intensity ribbon blender to provide a homogeneous powder. The resulting powder is allowed to set for a period of time sufficient to permit entrapped air to escape. The deareated power is then pelletize in a conventional pelleting machine. In an aspect of the invention, the deaerated powder is compressed at a pressure of from about 1,000 to about 7,500 psi and in an aspect of the invention, the deaerated powder is compressed at a pressure of from about 2,000 to about 4,000 psi.

In some embodiments, the compressed tablet is coated, while in other embodiments the compressed tablet is uncoated.

Example 1

Breath Mint

| Ingredient | Wt % |
|---|---|
| Natural peppermint powder | 35.7 |
| N-Ethyl-p-menthane-3-carboxamide | 4.8 |
| Xylitol | 11.4 |
| Sucralose | 2.1 |
| High viscosity hydroxypropyl methylcellulose (Methocel 100K) | 17.6 |
| Low viscosity hydroxypropyl methylcellulose (Methocel K4M) | 8.8 |
| Hydroxypropylcellulose (Klucel Nutra D) | 5.3 |
| Sodium alginate (Keltrone HVCR, NF) | 7.3 |
| Magnesium stearate | 2.3 |

The ingredients were blended and tableted into 6.4 mm (0.25 in) diameter by 4.4 mm thick, 141 mg tablets. The tablets took at least about 2 hours to dissolve when attached to a user's gum.

A breath mint was prepared by blending the all the ingredients in a high intensity ribbon blender to provide a homogeneous powder. The resulting powder was allowed to set for twelve hours until the entrapped air escapes. The deareated powder was then pelletized in a pelleting machine at a pressure of from about 4,000 psi to produce a breath mint weighing 141 mg and having circular cross section with a diameter of 6.4 mm.

Example 2

Breath Mint

| Ingredient | Wt % |
|---|---|
| Peppermint flavor | 35.7 |
| N-Ethyl-p-menthane-3-carboxamide | 4.8 |
| Xylitol | 11.4 |
| Sucralose | 2.1 |
| Hypromellose | 26.6 |
| Hydroxypropylcellulose | 5.3 |

-continued

| Ingredient | Wt % |
|---|---|
| Sodium alginate | 7.3 |
| Magnesium stearate | 2.3 |

Paddle Test

A paddle test was conducted to quantify the slow dissolution of the breath mint of the invention. A 250 ml beaker containing a stir bar and 200 ml of deionized water at pH 6.4 was placed inside a water bath (600 ml beaker filled with ~150 ml of H2O). A thermometer was taped to the inside of the 600 ml beaker to monitor the temperature of the water bath. The entire apparatus was placed on a Corning Hot Plate Stirrer (Model PC---220). Stirring was set to 60 cycles per minute and the temperature of the water bath was equilibrated to 37 C. Once these conditions were stable (60 cycles/min, 37 C), the breath mint was placed in the 250 ml beaker as a timer was started and the start time was recorded in a lab notebook. It took over 18 hours for the breath mint to dissolve.

As a comparison, existing mints available on the market were also analyzed using a dissolution test. As can be seen from the test results below, the mints of the invention had a much greater life.

| ANALYSIS | METHOD | MDL | |
|---|---|---|---|
| Dissolution | ARL 2.27* | 1.0 | |
| ARL ID | Description | RESULT | UOM |
| 106017 | Mints of the invention | 240 | Minutes |
| 106012 | Tic Tac Freshmints | 26 | Minutes |
| 106016 | Mintos | 18 | Minutes |
| 106014 | Altoids Wintegreen Small | 17.75 | Minutes |
| 106015 | Breath Savers Peppermint | 16.5 | Minutes |
| 106013 | Icebreakers | 9.75 | Minutes |

Notes:
*60 cycles per minute, 37.4C, pH 6.44.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A method of freshening breath of a user comprising the steps of:
    placing a tablet in the mouth of the user, said tablet comprising a carrier and a flavorant;
    wetting said tablet with saliva;
    converting a surface of said tablet to a gel resulting in an outer gel layer and a core;
    slowing exposure of said core to moisture with said gel; and
    slowing diffusion of said flavorant into the mouth of the user with said gel,
    wherein said step of slowing exposure comprises diffusing said flavorant through said gel for greater than 30 minutes,
    and wherein said gel comprises at least one of a high viscosity cellulose ether and low viscosity cellulose ether and an alginate.

2. The method according to claim 1 further comprising the step of:
    molding said gel layer to a mouth structure for assisting in adhering said tablet to said mouth structure with said gel.

3. The method according to claim 1 wherein said step of slowing exposure comprises: diffusing flavorant through said gel for greater than 1 hour.

4. The method according to claim 3 wherein said step of slowing exposure comprises:
    diffusing said flavorant through said gel for greater than 2 hours.

5. The method according to claim 1 wherein:
    said tablet further comprises an enhancer; and
    wherein said method further comprises a step of diffusing said enhancer through said gel.

6. The method according to claim 5 wherein:
    said enhancer is selected from a group consisting of vitamin D, chromium picolinate, Xylitol, vitamin B complex, and melatonin.

* * * * *